United States Patent [19]

Perkins et al.

[11] Patent Number: 5,597,936
[45] Date of Patent: Jan. 28, 1997

[54] METHOD FOR MANUFACTURING COBALT CATALYSTS

[75] Inventors: Christopher M. Perkins, Cincinnati; Mark R. Sivik, Fairfield, both of Ohio

[73] Assignee: The Procter & Gamble Company, Cincinnati, Ohio

[21] Appl. No.: 508,198

[22] Filed: Jul. 27, 1995

Related U.S. Application Data

[63] Continuation-in-part of Ser. No. 491,185, Jun. 16, 1995, abandoned.

[51] Int. Cl.⁶ ........................................... C07F 15/06
[52] U.S. Cl. .................. 556/148; 556/9; 556/7; 556/16; 556/24; 556/74
[58] Field of Search .................. 556/648, 24, 9, 556/7, 16, 74

[56] References Cited

U.S. PATENT DOCUMENTS

| | | | |
|---|---|---|---|
| 4,218,377 | 8/1980 | Stockinger et al. | 556/148 X |
| 4,325,884 | 4/1982 | Kang | 556/148 |
| 4,364,871 | 12/1982 | Svatek et al. | 556/148 |
| 4,425,278 | 1/1984 | Wirth et al. | 554/74 |
| 4,430,243 | 2/1984 | Bragg . | |
| 4,810,410 | 3/1989 | Diakun et al. . | |
| 4,915,854 | 4/1990 | Mao et al. . | |
| 5,114,611 | 5/1992 | Van Kralingen et al. . | |
| 5,173,207 | 12/1992 | Drapier et al. . | |
| 5,244,594 | 9/1993 | Favre et al. . | |
| 5,246,612 | 9/1993 | Van Dijk et al. . | |

FOREIGN PATENT DOCUMENTS

| | | |
|---|---|---|
| 408131 | 1/1991 | European Pat. Off. . |
| 549271 | 6/1993 | European Pat. Off. . |
| 2054109 | 10/1971 | Germany . |

OTHER PUBLICATIONS

Tobe, *Adv. Inorg.–Bioinorg. Mech.*, vol. 2, No. 1, 1983, pp. 1–94.
Williams et al., *J. of Chem. Ed.*, vol. 66, No. 12, Dec. 1989, pp. 1043–1045.
Jolly, *The Synthesis and Characterization of Inorganic Compounds*, Prentice–Hall, Inc., N.J., 1970, pp. 460–463.
Jackman et al., *Inorg. Chem.*, vol. 18, No. 6, 1979, pp. 1497–1502.
Wierenga et al., *Inorg. Chem.*, vol. 21, 1982, pp. 2881–2885.
Jackman et al., *Inorg. Chem.*, vol. 18, No. 7, pp. 2023–2025.
Chan et al., *Aust. J. Chem.*, vol. 20, 1957, pp. 2529–2531.
Rochow, *Inorganic Synthesis*, vol. 6, McGraw–Hill Book Co., Inc., N.Y., 1960, pp. 172–175.
Bailar, *Inorganic Syntheses*, vol. 4, McGraw–Hill Book Co., Inc., N.Y., 1953, pp. 170–177.

*Primary Examiner*—Paul F. Shaver
*Attorney, Agent, or Firm*—K. W. Zerby; J. J. Yetter; J. C. Rasser

[57] ABSTRACT

A method for manufacturing cobalt complexes having the formula:

$$[Co(NH_3)_5M]T_y$$

wherein M ligands are selected from substituted and unsubstituted $C_1$–$C_{30}$ carboxylic acids having the formulas:

$$RC(O)O-;$$

said method comprising reacting cobalt (II) complexes having the formula $[Co(H_2O)_6] T_y$, (e.g., T is chloride) with concentrated ammonium hydroxide/ammonium chloride, followed by an oxidizing agent (e.g., peroxide), followed by carboxylic acid anhydride of the formula $RC(O)O(O)CR$.

16 Claims, No Drawings

METHOD FOR MANUFACTURING COBALT CATALYSTS

CROSS REFERENCE TO RELATED APPLICATION

This is a continuation-in-part application of U.S. application Ser. No. 08/491,185, filed Jun. 16, 1995 now abandoned, by Perkins.

TECHNICAL FIELD

The present invention relates to methods for manufacturing cobalt complexes having the formula:

$[Co(NH_3)_5M]T_y$ wherein M ligand is selected from substituted and unsubstituted $C_1$–$C_{30}$ carboxylic acids having the formula:

$RC(O)O-$.

These catalysts are particularly useful in bleach-containing consumer compositions, especially automatic dishwashing detergents and laundry detergents comprising bleach.

BACKGROUND OF THE INVENTION

Cobalt catalysts are well known, as are a variety of methods for manufacturing them. Most synthesis methods, however, are directed simply to methods effective for obtaining experimental quantities for academic studies. These are described, for example, in M. L. Tobe, "Base Hydrolysis of Transition-Metal Complexes", *Adv. Inorg. Bioinorg. Mech.*, (1983), 2, pages 1–94; *J. Chem. Ed.* (1989), 66 (12), 1043–45; "The Synthesis and Characterization of Inorganic Compounds", W. L. Jolly (Prentice-Hall; 1970), pp. 461–3; *Inorg. Chem.*, 18, 1497–1502 (1979); *Inorg. Chem.*, 21, 2881–2885 (1982); *Inorg. Chem.*, 18, 2023–2025 (1979); *Inorg. Synthesis*, 173–176 (1960); and *Journal of Physical Chemistry*, 56, 22–25 (1952).

For use in consumer products, however, it is necessary that the cobalt catalysts be prepared in large quantities by the most cost effective manner with the highest possible purity. It has been discovered by the present invention that cobalt catalysts containing carboxylate ligands can be prepared on an industrially useful scale by the present process.

BACKGROUND ART

U.S. Pat. No. 4,810,410, to Diakun et al, issued Mar. 7, 1989; U.S. Pat. No. 5,246,612, to Van Dijk et al., issued Sep. 21, 1993; U.S. Pat. No. 5,244,594, to Favre et al., issued Sep. 14, 1993; and European Patent Application, Publication No. 408,131, published Jan. 16, 1991 by Unilever NV, see also: U.S. Pat. No. 5,114,611, to Van Kralingen et al, issued May 19, 1992 (transition metal complex of a transition metal, such as cobalt, and a non-macro-cyclic ligand); U.S. Pat. No. 4,430,243, to Bragg, issued Feb. 7, 1984 (laundry bleaching compositions comprising catalytic heavy metal cations, including cobalt); German Patent Specification 2,054,019, published Oct. 7, 1971 by Unilever N.V. (cobalt chelant catalyst); and European Patent Application Publication No. 549,271, published Jun. 30, 1993 by Unilever PLC (macrocyclic organic ligands in cleaning compositions).

SUMMARY OF THE INVENTION

The present invention relates to methods for manufacturing cobalt complexes having the formula:

$[Co(NH_3)_5M]T_y$ wherein the M ligand is selected from substituted and unsubstituted $C_1$–$C_{30}$ carboxylic acids having the formula:

$RC(O)O-$;

said method comprising the steps of:

(a) reacting a cobalt (II) salt having the formula:

$[Co(H_2O)_6]T_y$ wherein T is one or more counteranions present in a number y to obtain a charge-balanced salt (preferred T are selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof); and y is 1 or 2;

with concentrated ammonium hydroxide and ammonium chloride; followed by (b) reacting the product of step (a) with an oxidizing agent selected from the group consisting of oxygen, hydrogen peroxide, and mixtures thereof; followed by (c) reacting the product of step (b) with a carboxylic acid anhydride of the formula:

$RC(O)O(O)CR$ wherein each R is independently selected from substituted or unsubstituted $C_1$–$C_{30}$ moieties (preferably both R are the same);

(d) optionally, exchanging one T counterion with another T counterion; and (e) collecting the cobalt complex.

All pans, percentages and ratios used herein are expressed as percent weight unless otherwise specified. All documents cited are, in relevant pan, incorporated herein by reference.

DETAILED DESCRIPTION OF THE INVENTION

The present invention relates to a method for manufacturing cobalt complexes having the formula:

$[Co(NH_3)_5M]T_y$ wherein the M ligands are selected from substituted and unsubstituted $C_1$–$C_{30}$ carboxylic acids having the formulas:

$RC(O)O-$.

This method comprises the first step of reacting a cobalt (II) salt having the formula:

$[Co(H_2O)_6]T_y$ wherein T is one or more counteranions present in a number y to obtain a charge-balanced salt (preferred T are selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof); y is 1 or 2;

with concentrated ammonium hydroxide and ammonium chloride (preferably at least 20%, more preferably at least 25%, and typically between 28–32% solutions of concentrated ammonium hydroxide). This step is typically conducted at room temperature; preferred temperatures are below about 90° C., more preferably below 80° C. Preferred is to use from about 5.0 to about 10.0 equivalents, more preferably from about 5.0 to about 5.5 equivalents, of ammonium hydroxide in a concentrated aqueous solution so as to minimize the volume of water present during the reaction.

This first step is followed by a step whereby the product of the first step is reacted with an oxidizing agent selected from the group consisting of an oxidizing source such as oxygen and, especially, hydrogen peroxide (preferably at concentrations of at least about 30% and more preferably at least about 50% by weight). This step is also typically conducted at room temperature; preferred temperatures are below about 90° C., more preferably below 80° C.

This reaction step is then followed by reacting the product of the previous step with a carboxylic acid anhydride of the formula:

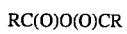

RC(O)O(O)CR wherein each R is independently selected from substituted or unsubstituted $C_1$–$C_{30}$ moieties. It is preferred that both R moieties are the same, but mixed anhydrides may be used as desired for the desired cobalt complex being synthesized. Reaction conditions for this step are typically room temperature (preferred temperatures are below about 90° C., more preferably below 80° C.) for from about 10 to about 60 minutes. Additionally, about 1.0 to about 2.0 equivalents of the ammonium carboxylate salt can be added prior to the addition of the carboxylic acid anhydride to facilitate synthesis of the desired cobalt complex.

This reaction step is then optionally followed by exchanging the T counterion of the prepared cobalt complex with another T counterion. This may be carried out, for example, by treating the complex with an acid (e.g., HCl or $HClO_4$), or a salt (e.g., $NaPF_6$).

At the end of the reaction process, the mixture is optionally filtered and the cobalt complex is collected. Preferred collection methods include, for example, evaporation to remove the solvent or lyophilization or precipitation (e.g., by addition of a co-solvent). The cobalt complex collected may be used as is, or further purified or modified for incorporation into the desired product or use to be made of the complex. This includes optionally washing the solid product with a suitable solvent, e.g., ethanol, to remove non-cobalt salts.

The present invention method preferably is carried out in one reaction vessel without isolation or separation of the intermediate reaction products. However, if desired, one or more of the reaction steps may be conducted in separate reaction vessels, and may be followed or preceded by optional separation and/or collection steps of the intermediate reaction materials.

Preferred T are selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof. Optionally, T can be protonated if more than one anionic group exists in T, e.g., $HPO_4^{2-}$, $HCO_3^-$, $H_2PO_4^-$, etc. Further, T may be selected from the group consisting of non-traditional inorganic anions such as anionic surfactants (e.g., linear alkylbenzene sulfonates (LAS), alkyl sulfates (AS), alkylethoxysulfonates (AES), etc.) and/or anionic polymers (e.g., polyacrylates, polymethacrylates, etc.).

Herein, R is preferably selected from the group consisting of hydrogen and $C_1$–$C_{30}$ (preferably $C_1$–$C_{18}$) unsubstituted and substituted alkyl, $C_6$–$C_{30}$ (preferably $C_6$–$C_{18}$) unsubstituted and substituted aryl, and $C_3$–$C_{30}$ (preferably $C_5$–$C_{18}$) unsubstituted and substituted heteroaryl, wherein substituents are selected from the group consisting of —$NR'_3$, —$NR'_4{}^+$, —C(O)OR', —OR', —C(O)$NR'_2$, wherein R' is selected from the group consisting of hydrogen and $C_1$–$C_6$ moieties. Such substituted R therefore include the moieties —$(CH_2)_n OH$ and —$(CH_2)_n NR'_4{}^+$, wherein n is an integer from 1 to about 16, preferably from about 2 to about 10, and most preferably from about 2 to about 5.

Most preferred M are carboxylic acids having the formula above wherein R is selected from the group consisting of hydrogen, methyl, ethyl, propyl, straight or branched $C_4$–$C_{12}$ alkyl, and benzyl. Most preferred R is methyl. The M moieties include mono-carboxylates, which are preferred, but more than one carboxylate may be present in the moiety as long as the binding to the cobalt is by only one carboxylate per moiety (in which case the other carboxylate in the M moiety may be protonated or in its salt form). Preferred carboxylic acid M moieties include formic, benzoic, octanoic, nonanoic, decanoic, dodecanoic, malonic, maleic, succinic, adipic, phthalic, 2-ethylhexanoic, naphthenoic, oleic, palmitic, triflate, tartrate, stearic, butyric, citric, acrylic, aspartic, fumaric, lauric, linoleic, lactic, malic, and especially acetic acid. Therefore, most preferred methods use the anhydrides comprising these carboxylic acids, and preferred anhydrides are the same acids. Most preferred anhydride is acetic anhydride.

The preferred cobalt complexes prepared by the present invention are cobalt(III) pentaamineacetate dichloride, i.e. $[Co(NH_3)_5 OAc]Cl_2$ (herein "PAC"); cobalt(III) pentaamineacetate diacetate, i.e. $[Co(NH_3)_5 OAc](OAc)_2$; $[Co(NH_3)_5 OAc](PF_6)_2$; $[Co(NH_3)_5 OAc](SO_4)$; and $[Co(NH_3)_5 OAc](BF_4)_2$.

The starting cobalt(II) complexes useful herein, the $[Co(H_2O)_6]T_y$ complexes, are commercially available and can be prepared by a variety of methods.

The following nonlimiting examples further illustrate the method according to the present invention.

EXAMPLE 1

Synthesis of $[Co(NH_3)_5 OAc]Cl_2$ (designated as "PAC")

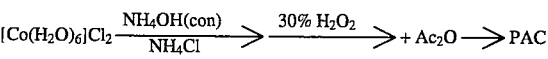

$[Co(H_2O)_6]Cl_2 \xrightarrow{\frac{NH_4OH(con)}{NH_4Cl}} \xrightarrow{30\% H_2O_2} + Ac_2O \longrightarrow PAC$ $NH_4Cl$ (25.0 g) is dissolved in $NH_4OH$ (150 mL). $[Co(H_2O)_6]Cl_2$ (26.4 g, 0.10 mol) is added to this solution forming a slurry. $H_2O_2$ (30%, 40.0 mL) is slowly dripped into the solution with stirring. Acetic anhydride (30.6 g, 0.30 mol) is slowly added with stirring. The solution is stirred 1 hour at RT. At this point the reaction solution can either be lyophilized to a pink powder or the solution can be rotovapped down and the resulting solid pumped on overnight at 0.05 mm. to remove residual water and $NH_4 OAc$. The excess ammonium acetate and ammonium chloride salts can also be removed by washing the solid with ethanol. Yield 35 gr., 78.1% by UV-Vis spectroscopy. HPLC [according to the method of D. A. Buckingham, et al, *Inorg. Chem.*, 28, 4567–4574 (1989)] shows all of the cobalt is present as $[Co(NH_3)_5 OAc]Cl_2$.

EXAMPLE 2

Synthesis of $[Co(NH_3)_5 OAc]Cl_2$

Ammonium hydroxide (4498.0 mL, 32.3 mol, 28%) and ammonium chloride (749.8 g, 14.0 mol) are combined in a 12 L three-necked round-bottomed flask fitted with a condenser, internal thermometer, mechanical stirrer, and addition funnel. Once the mixture becomes homogeneous, cobalt(II) chloride hexahydrate (1500.0 g, 6.3 tool) is added in portions over 5 rain forming a slurry. The reaction mixture warms to 50° C and takes on a muddy color. $H_2O_2$ (429.0 g, 6.3 mol, 50%) is added over 30 min. The mixture becomes deep red and homogeneous and the temperature raises to 60°–65° C. during addition of the peroxide. Ammonium acetate (485.9 g, 6.3 mol) is then added to the mixture 30 min later. After stirring an additional 15 min, acetic anhydride (2242.5 g, 22.1 mol) is added over 1 h. The anhydride is added so as to keep the reaction temperature below 75° C. The mixture is stirred for 2 h as it cools. The red mixture is filtered and the filtrate treated with isopropanol until an orange-pink solid forms. The solid is collected, washed with isopropanol, ether, and dried to give an orange-pink solid. UV-Vis measurements indicate the product to be 95.3% pure as $[Co(NH_3)_5OAc]Cl_2$.

What is claimed is:

1. A method for manufacturing cobalt complexes having the formula:

$$[Co(NH_3)_5M]T_y$$

wherein the M ligand is selected from substituted and unsubstituted $C_1$–$C_{30}$ carboxylic acids having the formula:

$$RC(O)O\text{—};$$

said method comprising the steps of:

(a) reacting a cobalt (II) salt having the formula:

$$[Co(H_2O)_6]T_y$$

wherein T is one or more counteranions present in a number y to obtain a charge-balanced salt; and y is 1 or 2;

with concentrated ammonium hydroxide and ammonium chloride; followed by (b) reacting the product of step (a) with an oxidizing agent selected from the group consisting of oxygen, hydrogen peroxide, and mixtures thereof; followed by (c) reacting the product of step (b) with a carboxylic acid anhydride of the formula:

$$RC(O)O(O)CR$$

wherein each R is independently selected from substituted or unsubstituted $C_1$–$C_{30}$ moieties;

(d) optionally, exchanging one T counterion with another T counterion; and (e) collecting the cobalt complex.

2. The method according to claim 1 wherein T is selected from the group consisting of chloride, iodide, $I_3^-$, formate, nitrate, nitrite, sulfate, sulfite, citrate, acetate, carbonate, bromide, $PF_6^-$, $BF_4^-$, $B(Ph)_4^-$, phosphate, phosphite, silicate, tosylate, methanesulfonate, and combinations thereof.

3. The method according to claim 1 wherein the concentrated ammonium hydroxide is at least about 25% ammonium hydroxide.

4. The method according to claim 3 utilizing from about 5.0 to about 10.0 equivalents of ammonium hydroxide in a concentrated aqueous solution.

5. The method according to claim 1 wherein each R in the anhydride is independently selected from the group consisting of hydrogen and $C_1$–$C_{30}$ unsubstituted and substituted alkyl, $C_6$–$C_{30}$ unsubstituted and substituted aryl, and $C_3$–$C_{30}$ unsubstituted and substituted heteroaryl, wherein substituents are selected from the group consisting of —$NR'_3$, —$NR'_4{}^+$, —$C(O)OR'$, —$OR'$, —$C(O)NR'_2$, wherein R' is selected from the group consisting of hydrogen and $C_1$–$C_6$ moieties.

6. The method according to claim 5 wherein each R in the anhydride is independently selected from $C_1$–$C_{18}$ unsubstituted and substituted alkyl.

7. The method according to claim 6 wherein each R in the anhydride is independently selected from the group consisting of hydrogen, methyl, ethyl, propyl, straight or branched $C_4$–$C_{12}$ alkyl, and benzyl.

8. The method according to claim 7 wherein R is methyl.

9. The method according to claim 6 wherein each R is independently selected from the moieties —$(CH_2)_nOH$ and —$(CH_2)_nNR'_4{}^+$, wherein n is an integer from 1 to about 16.

10. The method according to claim 1 wherein the M ligand is a carboxylic acid moiety selected from formic, benzoic, octanoic, nonanoic, decanoic, dodecanoic, malonic, maleic, succinic, adipic, phthalic, 2-ethylhexanoic, naphthenoic, oleic, palmitic, triflate, tartrate, stearic, butyric, citric, acrylic, aspartic, fumaric, lauric, linoleic, lactic, malic, and acetic acid.

11. The method according to claim 10 wherein M is an acetic acid moiety.

12. A method for manufacturing cobalt complexes having the formula:

$$[Co(NH_3)_5M]T_y$$

wherein the M ligand is selected from substituted and unsubstituted $C_1$–$C_{30}$ carboxylic acids having the formula:

$$RC(O)O\text{—};$$

wherein R is selected from $C_1$–$C_{18}$ unsubstituted and substituted alkyl moieties;

said method comprising the steps of:

(a) reacting a cobalt (II) salt having the formula:

$$[Co(H_2O)_6]T_y$$

wherein T is one or more counteranions present in a number y to obtain a charge-balanced salt; and y is 1 or 2;

with concentrated ammonium hydroxide and ammonium chloride; followed by (b) reacting the product of step (a) with hydrogen peroxide; followed by (c) reacting the product of step (b) with a carboxylic acid anhydride of the formula:

$$RC(O)O(O)CR$$

wherein each R is independently selected from $C_1$–$C_{18}$ unsubstituted and substituted alkyl moieties; and (d) optionally, exchanging one T counterion with another T counterion; and (e) collecting the cobalt complex.

13. The method according to claim 12 wherein both R in the anhydride are the same moiety selected from the group consisting of hydrogen, methyl, ethyl, propyl, straight or branched $C_4$–$C_{12}$ alkyl, and benzyl.

14. The method according to claim 13 wherein the anhydride is acetic anhydride.

15. The method according to claim 12 wherein each R in the anhydride is independently selected from the moieties —$(CH_2)_n$OH and —$(CH_2)_n NR'^{+}_4$, wherein n is an integer from about 2 to about 10.

16. The method according to claim 12 utilizing from about 5.0 to about 10.0 equivalents of ammonium hydroxide in a concentrated aqueous solution.

* * * * *